(12) United States Patent
Mouyen

(10) Patent No.: US 6,851,852 B1
(45) Date of Patent: Feb. 8, 2005

(54) METHOD FOR OBTAINING A RADIOGRAPHIC IMAGE OF A TOOTH AND ITS SURROUNDING ENVIRONMENT, AND DEVICES IMPLEMENTING SAID METHOD

(75) Inventor: Francis Mouyen, Pas-de-la-Case (AD)

(73) Assignee: Trophy Radiologie, Beaubourg (FR)

(*) Notice: Subject to any disclaimer, the term of this patent is extended or adjusted under 35 U.S.C. 154(b) by 0 days.

(21) Appl. No.: 10/049,597

(22) PCT Filed: Aug. 29, 2000

(86) PCT No.: PCT/FR00/02398

§ 371 (c)(1),
(2), (4) Date: Feb. 14, 2002

(87) PCT Pub. No.: WO01/15603

PCT Pub. Date: Mar. 8, 2001

(30) Foreign Application Priority Data

Aug. 30, 1999 (FR) .......................... 99 10911

(51) Int. Cl.[7] ............................... A61B 6/14
(52) U.S. Cl. .................. 378/191; 378/98.8; 250/368; 250/370.11
(58) Field of Search .................... 378/98.8, 168, 378/169, 191; 250/370.09, 370.11, 367, 368, 369

(56) References Cited

U.S. PATENT DOCUMENTS

| 4,995,062 A | * | 2/1991 | Schulze-Ganzlin et al. ... 378/22 |
| 5,382,798 A | * | 1/1995 | Mouyen ................ 250/370.11 |
| 5,434,418 A | | 7/1995 | Schick ................. 250/370.11 |
| 6,030,119 A | * | 2/2000 | Tachibana et al. .......... 378/169 |

FOREIGN PATENT DOCUMENTS

| DE | 44 41 939 A1 | 6/1995 |
| EP | 0 357 944 A1 | 3/1990 |
| EP | 0 413 043 A1 | 2/1991 |
| EP | 0 756 416 A1 | 1/1997 |

* cited by examiner

Primary Examiner—Edward J. Glick
Assistant Examiner—Courtney Thomas

(57) ABSTRACT

The invention concerns methods and devices for obtaining a radiographic image of a tooth and its surrounding environment. The method and the device are essentially characterized in that cylindrical rods produced from a material capable of transforming X-rays into light rays are arranged side by side for receiving the X-rays emitted by a source after they have passed through the tooth and its surrounding environment so as to both guide them and transform them into light rays, means thereafter converting said light rays into electric signals which are processed to produce the radiographic image.

10 Claims, 1 Drawing Sheet

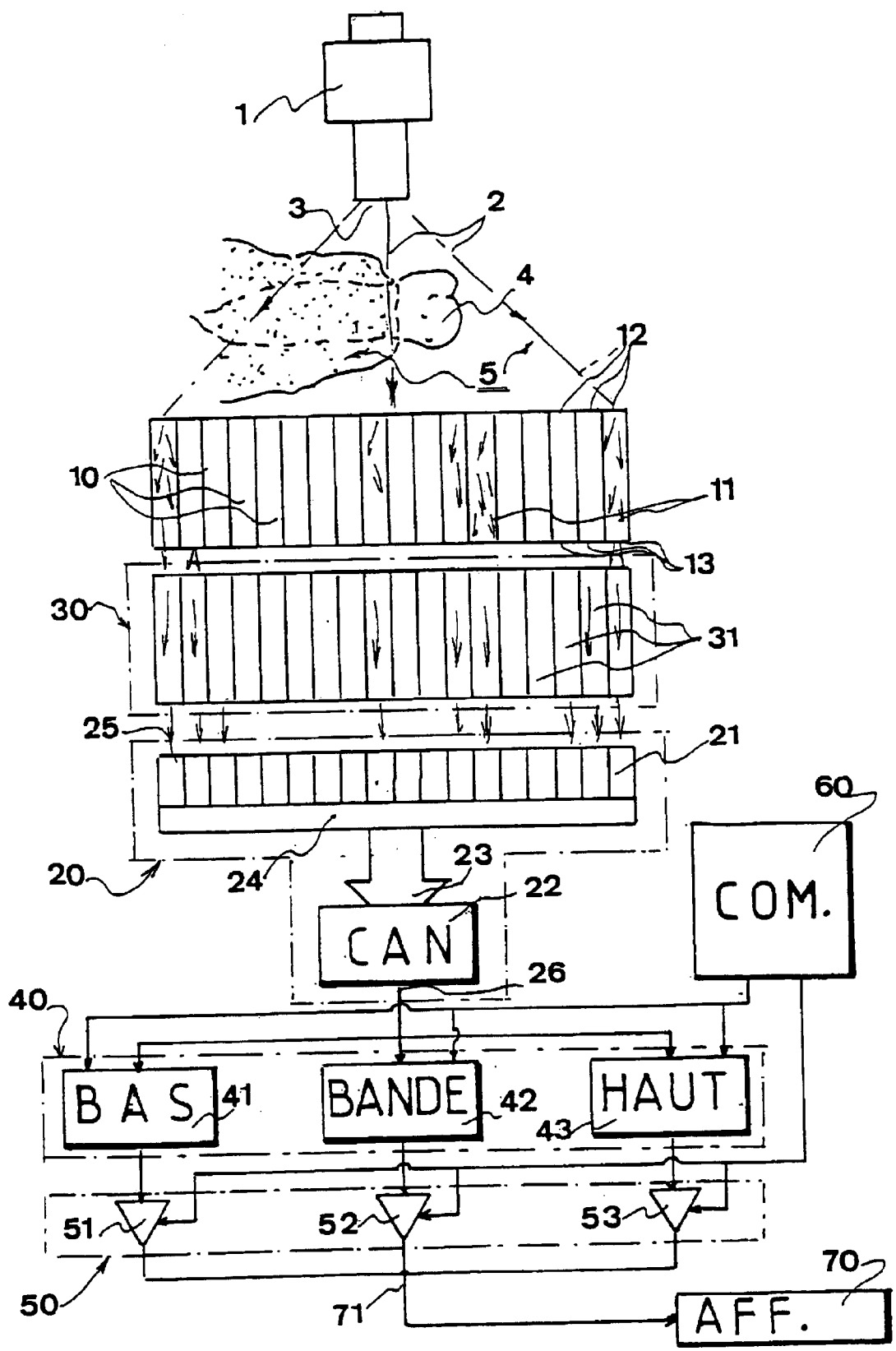

METHOD FOR OBTAINING A RADIOGRAPHIC IMAGE OF A TOOTH AND ITS SURROUNDING ENVIRONMENT, AND DEVICES IMPLEMENTING SAID METHOD

This application is the national phase under 35 U.S.C. § 371 of PCT International Application No. PCT/FR00/02398 which has an International filing date of Aug. 29, 2000, which designated the United States of America.

The invention relates to the techniques of dental radiology and concerns, more particularly, the methods of obtaining a radiographic image of a tooth and of its surrounding area, as well as the apparatuses for permitting these methods to be accomplished.

The evolution of electronics seen in these last years has permitted the techniques for radiological examinations of organs of the human body to be improved significantly. The aim of this evolution is, more particularly, to reduce, for the patient and for the operative, the doses of exposure to the X-rays while improving the image quality of the X-rayed target. The methods and the apparatuses described and illustrated in the French patents published under the numbers 2 333 404, 2 378 496, 2 415 938, 2 495 429, 2 476 949, 2 477 626, 2 479 636, 2 185 667, 2 247 749 and 2 310 059 demonstrate this state of affairs well.

The techniques of dental exploration have themselves remained at the traditional stage of radiography, which comprises inserting the tooth to be examined between an extra-buccal source of X-rays and an intra-buccal radiographic film sensitive to the X-rays which traverse the irradiated tooth. The forms of the image obtained on this radiographic film correspond to the shadows borne by the constituents which are more or less opaque to the X-rays of the examined tooth. Although this technique of dental radiography is the most common at the present time, it has the disadvantage, however, of limiting the number of plates, taking into account the X-ray doses which they require.

It is useful to specify that the new techniques of radiology have involved, more particularly, the intrinsic ability of the sensor of the bundle of X-rays emerging from the irradiated target in order, as has been mentioned above, to reduce the times of exposure to the X-rays, while improving the image quality of the X-rayed target. In addition, the image is obtained in real time, thereby avoiding the manipulations in developing the film of traditional dental radiography.

Such apparatuses are already known, for example the one which is described and illustrated in U.S. Pat. No. 4,160,997 (SCHWARTZ).

The intra-buccal sensor described in this American patent has numerous disadvantages, however, in particular the major disadvantage of not being able to fulfil its essential function which comprises recording the bundle of X-rays emerging from an irradiated tooth and to provide therefrom information capable of being analysed by an electronic processing unit, and this being in order to reveal, on the monitor of a display channel, the image of the aforesaid tooth. In fact, to understand that this intra-buccal sensor is not functional, it is useful to recall that the apparatuses for transferring charges have the following characteristics:

the dimensions of their sensitive face are not sufficient to detect all of the X-rays of a bundle emerging from an irradiated tooth, and SCHWARTZ propose to use, in their intra-buccal sensor, a screen which ensures a linear transmission, their sensitive face deteriorates under the impact of X-rays of greater power than 1 KeV, and the screen belonging to SCHWARTZ does not ensure sufficient protection for this sensitive face, the unit for the electronic processing of the electrical information coming from the charge-transferring apparatus does not have to be further away from the latter than twenty centimeters, this distance being the limit beyond which the output signal is too weak to be processed, and the unit for electronically processing the information at the output by of the SCHWARTZ intra-buccal sensor is extra-buccal and connected thereto by a cable longer than twenty centimeters.

Drawing up the balance sheet for this state of affairs, the Applicants carried out research which ended in the manufacture of an apparatus which permits a dental radiological image to be obtained on a monitor of a display channel and the aforementioned disadvantages to be overcome, in order to provide a functional apparatus with indisputable performance in the quality of reproduction of the dental image and in the reduction of the amount of exposure to the X-rays. The Applicants have already filed a patent application in this field, the application EP 0 129 451.

The present invention is the up-to-date result of their studies in the field. Its object is to improve the known methods of prior art to obtain a radiographic image of a tooth and of its surrounding area, as well as apparatuses which permit these methods to be accomplished.

More precisely, the present invention relates to a method of obtaining a radiographic image of a tooth and of its surrounding area, characterised in that it comprises:

emitting a bundle of X-rays in the direction of said tooth and its surrounding area, guiding the X-rays, which emerge from said tooth and its surrounding area, in substantially cylindrical volumes substantially along the axis of said volumes, transforming the X-rays, when they are guided in said cylindrical volumes, into light rays of a greater wavelength than that of the X-rays, converting these light rays into electrical signals, and processing these electrical signals to produce said radiographic image.

The present invention also relates to an apparatus for accomplishing the above method, characterised in that it comprises:

a source, which is capable of emitting a bundle of X-rays towards said tooth and its surrounding area, a plurality of cylindrical rods, which are produced from a material capable of transforming the X-rays into light rays of a wavelength greater than that of the X-rays, each rod comprising an inlet face, which is capable of receiving said X-rays, and an outlet face, which is capable of emitting said light rays, said cylindrical rods being disposed side by side so that all of the inlet faces are turned towards said X-ray source, means for converting light rays into electrical signals, means for connecting the outlet faces of the cylindrical rods to said means for converting light rays into electrical signals, and means for processing said electrical signals with a view to producing said radiographic image.

Other features and advantages of the present invention will appear in the course of the following description, given by way of example but in no way limiting, with reference to the accompanying drawing, in which:

The single FIGURE is the basic diagram of an apparatus according to the invention to obtain a radiographic image of a tooth and its surrounding area.

The present invention relates to a method of obtaining a radiographic image of a tooth and of its surrounding area, that is to say the gum portion in which the tooth is implanted, possibly even the jawbone, the possible cavities which such a tooth may comprise, filled or not with an amalgam or the like, etc.

The method essentially comprises emitting a bundle of X-rays in the direction of the tooth and its surrounding area. The X-rays, which emerge from the tooth and its surrounding area, are guided in substantially cylindrical volumes substantially along the axis of these volumes, while being transformed into light rays of a much greater wavelength than that of the X-rays, and such wavelength being selected so as to permit the conversion of these light rays into electrical signals.

The method finally comprises processing these electrical signals to produce the radiographic image, for example in the form of a video image or the like.

In a preferred embodiment, the method also comprises a stage which consists of filtering the electrical signals in dependence on predetermined criteria, for example, but not in a limiting manner, to eliminate the electrical signals which correspond to the images of the soft tissues of the gum or materials such as amalgams or the like, with the aim of only retaining the electrical signals which correspond to the images of the dentine.

These last signals may then be amplified according to a predetermined function, linear or not, to have, for example, only a portion of the image of the dentine dilated so that the dental practitioner can effect a more precise analysis of the state of the X-rayed tooth.

The method, the stages of which have been described above, is advantageously accomplished with an apparatus, the basic diagram of which is illustrated in the single FIGURE.

The apparatus, illustrated schematically in the single FIGURE, comprises an X-ray source 1, which is capable of emitting a bundle 2 of X-rays from an outlet aperture 3. This X-ray source 1 is capable of being positioned so that its outlet aperture is directed towards a tooth 4 and its surrounding area 5.

The apparatus also comprises a plurality of cylindrical rods 10, which are produced from a material capable of transforming the X-rays into light rays 11 of a wavelength greater than that of the X-rays.

Each rod comprises an inlet face 12, which is capable of receiving the X-rays from the bundle 2 after they have traversed the tooth 4 and its environment 5, and an outlet face, which is capable of emitting the light rays 11. These cylindrical rods 10 are disposed side by side so that all of the inlet faces 12 are turned towards the outlet aperture 3 of the X-ray source 1.

In an advantageous embodiment, the cylindrical rods 10 are produced in a caesium iodide crystal and have a substantially cylindrical revolving configuration, with a length of between 80 and 200 $\mu$m, preferably between 100 and 120 $\mu$m, for a diameter of between 3 and 7 $\mu$m, preferably between 4 and 6 $\mu$m.

In addition, it is certainly advantageous that, as illustrated in the single FIGURE, these cylindrical rods are in contact with one another to form in some manner a mosaic, the thickness of which is equal to the length of a rod.

The apparatus according to the invention has an essential advantage over previous apparatuses of the same type: the construction and the disposition of the cylindrical rods 10, such as described above, permit the X-rays, which penetrate into these rods through their inlet face 12, to be perfectly guided. The result is only a very weak dispersal of X-rays into the surrounding space, and this permits virtually all of the X-rays, which have traversed the tooth and its surrounding area, to be transformer into light rays, and hence permits the sensitivity of the apparatus to be increased very substantially as compared with apparatuses of the same type from known prior art.

The apparatus also comprises means 20 for converting the light rays 11 into electrical signals.

In a preferred embodiment, these means 20 comprise a converter 21 for converting light rays into analogue electrical signals and a converter 22 for converting analogue electrical signals into digital electrical signals, the inlet 23 of which latter converter is connected to the outlet 24 of the analogue converter 21.

Advantageously, the analogue converter 21 is formed by a CCD bar, while the digital converter 22 is a CAN converter of the type which has at least twelve bits. Alternatively, the analogue converter may be formed by a CMOS bar.

Of course, the apparatus comprises means 30 for connecting the outlet faces 13 of the cylindrical rods 10 to the photosensitive faces 25 of the analogue converter 21. These connecting means 30 may be formed by means for positioning the photosensitive faces 25 opposite outlet faces 13 of the rods. However, with an aim to design an easily manipulative apparatus, it may be advantageous for these connecting means 30 to be formed by a bundle of optical fibres, as schematically illustrated by 31 in the FIGURE, the inlet faces of the optical fibres being positioned opposite the outlet faces 13 of the rods, and their outlet faces being disposed opposite the photosensitive faces 25 of the converter 21.

Advantageously, in order to adapt the use of the apparatus more to the wishes of dental practitioners, the apparatus comprises controllable means 40 for filtering the electrical signals obtained at the outlet of the means 20 defined above, that is to say, in the embodiment schematically illustrated in the FIGURE, at the outlet 26 of the CAN digital converter 22.

The apparatus may have a single filter, the passing band of which may be adapted to the wishes of the practitioner.

As illustrated, this filter may advantageously be equivalent to an assembly, for example, of three filters. By way of example: a "low-pass" filter 41, a "band-pass" filter 42 and a "high-pass" filter 43.

The low-pass filter 41 is, for example, capable of eliminating the electrical signals generated by the X-rays after they have traversed the most opaque parts of the tooth 4 and its surrounding area 5, such as a cavity of the tooth filled with an amalgam or the like, a post and core planted in a root, etc.

The band-pass filter 42 is, for example, capable of only allowing the electrical signals generated by the X-rays to pass therethrough after they have traversed the dentine of the tooth 4 and the material parts of its surrounding area 5 substantially equivalent to the dentine.

The high-pass filter 43 is, for example, capable of eliminating the electrical signals generated by the X-rays after they have traversed the soft tissues or the like of the tooth and its surrounding area, for example the flesh of the gum.

Alternatively, said means 40 for filtering the electrical signals comprise at least one of the following three filters: a low-pass filter 41, which is capable of eliminating the electrical signals corresponding to the X-rays after they have traversed the most opaque parts of said tooth 4 and its surrounding area 5, a band-pass filter 42, which is capable of allowing the electrical signals corresponding to the X-rays to pass therethrough after they have traversed the dentine of the tooth and the material parts of its surrounding area substantially equivalent to this dentine, and a high-pass filter 43, which is capable of eliminating the electrical signals corresponding to the X-rays after they have traversed soft tissues or the like of the tooth and its surrounding area.

In addition, in an advantageous embodiment, the apparatus comprises means 50 for amplifying the electrical signals issued by the means 20 for converting the light rays 11 into electrical signals.

In the example illustrated, these amplification means 50 are formed by three controllable amplifiers 51, 52 and 53, the inlets of which are respectively connected to the outlets of the three filters 41, 42 and 43.

In this manner, the signals obtained at the outlet 44 of the filter means 40 may be amplified according to a predetermined function, for example linear to obtain a homothetic image, without distortion, of the radiographic image of the tooth 4 and its surrounding area 5. But it may be advantageous to select a non-linear function in order to obtain a magnifying effect on a selected portion of the radiographic image, with the aim of effecting a more precise analysis of the state of that portion.

Of course, the assembly of the three filters 41–43 and the three amplifiers 51–53 is advantageously directed by a control unit 60 of the computer or analogue type.

Finally, the apparatus comprises means 70 for processing the electrical signals obtained, in the illustrated example, at the outlet 71 of the amplifiers 51–53, with a view to producing the radiographic image of the tooth and its surrounding area. These means 70 for processing electrical signals may be of different types, for example made up of temporary or permanent memories or generally of a converter for converting electrical signals into video signals which are capable of being displayed on the screen of a monitor.

What is claimed is:

1. An intra-buccal sensor sensitive to x-rays of a first wavelength emerging from an irradiated tooth and comprising:
    a. means, comprising a plurality of cylindrical rods positioned side-by-side with each rod having a longitudinal axis, for both (i) guiding the x-rays emerging from the tooth substantially along the longitudinal axes of the cylindrical rods and (ii) transforming the guided x-rays into light rays of wavelength greater than the first wavelength, the cylindrical rods being produced from a material enabling both the guiding and the transformation of the x-rays; and
    b. a plurality of optical fibers connected to the cylindrical rods.

2. An intra-buccal sensor according to claim 1 further comprising means, connected to the plurality of optical fibers, for converting light rays to electrical signals.

3. An intra-buccal sensor according to claim 2 in which each of the cylindrical rods has an outlet face to which an optical fiber is connected.

4. An intra-buccal sensor according to claim 3 in which (i) each of the cylindrical rods further has an inlet face capable of receiving the x-rays and (ii) the outlet faces are capable of emitting the light rays.

5. An intra-buccal sensor according to claim 2 in which the converting means comprises a CCD.

6. An intra-buccal sensor according to claim 1 in which the cylindrical rods are produced from caesium iodide crystal.

7. An intra-buccal sensor according to claim 1 in which the cylindrical rods have substantially cylindrical revolving configuration, length between 80 to 200 $\mu$m, and diameter between 3 to 7 $\mu$m.

8. An intra-buccal sensor according to claim 1 in which the cylindrical rods form a mosaic.

9. An apparatus comprising an intra-buccal sensor sensitive to x-rays emerging from an irradiated tooth and its surrounding area and comprising:
    means comprising a plurality of cylindrical rods, positioned side-by-side, for both guiding and transforming the x-rays into light rays;
    a plurality of optical fibers connected to the cylindrical rods;
    means for converting the light rays into electrical signals, connected to the optical fibers; and
    means for filtering the electrical signals, so as to retain the electrical signals of selective parts of the tooth and its surrounding area.

10. The apparatus according to claim 9, wherein the means for filtering the electrical signals comprise at least one of the following three filters:
    a low-pass filter, which is capable of eliminating the electrical signals corresponding to the x-rays after they have traversed the most opaque parts of the tooth and its surrounding area;
    a band-pass filter, which is capable of passing through the electrical signal corresponding to the x-rays after they have traversed a dentine part of the tooth and material parts of its surrounding area substantially equivalent to the dentine; and
    a high-pass filter, which is capable of eliminating the electrical signals corresponding to the x-rays after they have traversed soft tissues and its surrounding area.

* * * * *